(12) United States Patent
Chen

(10) Patent No.: US 8,597,406 B2
(45) Date of Patent: Dec. 3, 2013

(54) ISORETICULAR METAL-ORGANIC FRAMEWORK OF THE FORMULA ZN$_4$O(FMA)$_3$

(75) Inventor: Banglin Chen, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 193 days.

(21) Appl. No.: 13/066,859

(22) Filed: Apr. 27, 2011

(65) Prior Publication Data

US 2011/0272031 A1 Nov. 10, 2011

Related U.S. Application Data

(60) Provisional application No. 61/343,324, filed on Apr. 27, 2010.

(51) Int. Cl.
*C07F 3/06* (2006.01)
*F17C 11/00* (2006.01)

(52) U.S. Cl.
USPC ............................................. 95/90; 556/118

(58) Field of Classification Search
USPC ......... 95/90, 900; 96/108; 502/400, 401, 526; 206/0.7; 556/1, 118, 131
See application file for complete search history.

(56) References Cited

U.S. PATENT DOCUMENTS

| 7,847,115 B2* | 12/2010 | Schubert et al. ............. 556/132 |
| 2006/0252641 A1* | 11/2006 | Yaghi et al. .................... 502/401 |
| 2007/0248852 A1 | 10/2007 | Mueller et al. ..................... 95/90 |
| 2007/0252641 A1 | 11/2007 | Goodnow et al. ............. 327/543 |
| 2009/0305040 A1* | 12/2009 | Schubert et al. ............. 428/402 |
| 2012/0115961 A1* | 5/2012 | Hafizovic et al. ............. 514/772 |

FOREIGN PATENT DOCUMENTS

| JP | 2003-342260 | 12/2003 |
| JP | 2004-161675 | 6/2004 |
| JP | 2004-305985 | 11/2004 |
| WO | WO 2008/000694 | 1/2008 |

OTHER PUBLICATIONS

Bauer, et al., "Influence of connectivity and porosity on ligand-based luminescence in zinc metal—organic framework," *J. Am. Chem. Soc.*, 129:7136-44, 2007.
Bourrelly, et al., "Different adsorption behaviors of methane and carbon dioxide in the isotypic nanoporous metal terephthalates MIL-53 and MIL-47," *J. Am. Chem. Soc.*, 127:13519-21, 2005.
Britt, et al., "Highly efficient separation of carbon dioxide by a metal-organic framework replete with open metal sites," *PNAS*, 106:20637-40, 2009.
Chandler, et al., "Microporous metal-organic frameworks formed in a stepwise manner from luminescent building blocks," *J. Am. Chem. Soc.*, 128:10403-12, 2006.

Chen, et al., "A luminescent microporous metal-organic framework for the recognition and sensing of anions," *J. Am. Chem. Soc.*, 6718-9, 2008.
Chen, et al., "A triply interpenetrated microporous metal-organic framework for selective sorption of gas molecules," *Inorg. Chem.*, 46:8490-2, 2007.
Chen, et al., "High H2 adsorption in a microporous metal-organic framework with open metal sites," *Angew. Chem. Int. Ed. Engl.*, 44:4745-9, 2005.
Chen, et al., "Luminescent open metal sites within a metal-organic framework for sensing small molecules," *Adv. Mater.*, 19:1693-6, 2007.
Chen, et al., "Multiroute synthesis of porous anionic frameworks and size-tunable extraframework organic cation-controlled gas sorption properties," *J. Am. Chem. Soc.*, 131:16027-9, 2009.
Chen, et al., "Rationally designed micropores within a metal-organic framework for selective sorption of gas molecules," *Inorg. Chem.*, 46:1233-6, 2007.
Chen, et al., "Selective gas sorption within a dynamic metal-organic framework," *Inorg. Chem.*, 46:9705-9, 2007.
Chen, et al., "Surface interactions and quantum kinetic molecular sieving for H2 and D2 adsorption on a mixed metal-organic framework material,"*J. Am. Chem. Soc.*, 130:6411-23, 2008.
Choi and Suh, "Highly selective CO$_2$ capture in flexible 3D coordination polymer networks," *Angew. Chem.*, 121:6997-7001, 2009.
Chui, et al., "A chemically functionalizable nanoporous material," *Science*, 283:1148-50, 1999.
Dietzel, et al., "Adsorption properties and structure of CO$_2$ adsorbed on open coordination sites of metal-organic framework Ni$_2$(dhtp) from gas adsorption, IR spectroscopy and X-ray diffraction," *Chem. Commun.*, pp. 5125-5127, 2008.
Dietzel, et al., "An in situ high-temperature single-crystal investigation of a dehydrated metal-organic framework compound and field-induced magnetization of one-dimensional metal-oxygen chains," *Angew. Chem. Int. Ed.*, 44:6354-8, 2005.
Dietzel, et al., "Hydrogen adsorption in a nickel based coordination polymer with open metal sites in the cylindrical cavities of the desolvated framework," *Chem. Commun.*, 959-61, 2006.
Dietzel, et al., "Structural changes and coordinatively unsaturated metal atoms on dehydration of honeycomb analogous microporous metal-organic frameworks," *Chemistry*, 14:2389-97, 2008.
Dină and Long, "Hydrogen storage in microporous metal-organic frameworks with exposed metal sites," *Angew. Chem. Int. Ed. Engl.*, 47:6766-79, 2008.
Eddaoudi, et al., "Modular chemistry: secondary building units as a basis for the design of highly porous and robust metal-organic carboxylate frameworks," *Acc. Chem. Res.*, 34:319-30, 2001.
Eddaoudi, et al., "Systematic design of pore size and functionality in isoreticular MOFs and their application in methane storage," *Science*, 295:469-72, 2002.

(Continued)

*Primary Examiner* — Frank Lawrence, Jr.
(74) *Attorney, Agent, or Firm* — Parker Highlander PLLC

(57) ABSTRACT

This invention provides metal-organic frameworks (MOFs) having repeat units of the formula Zn$_4$O(fumarate)$_3$. Also provided are compositions thereof and methods use thereof, including for gas storage, gas separation, catalysis and sensing.

13 Claims, 3 Drawing Sheets
(3 of 3 Drawing Sheet(s) Filed in Color)

(56) References Cited

OTHER PUBLICATIONS

Fang, et al., "A metal-organic framework with the zeolite MTN topology containing large cages of vol. 2.5 nm$^3$" *Angew. Chem. Int. Ed.*, 44:3845-8, 2005.

Fang, et al., "Mesoporous metal-organic framework with rare etb topology for hydrogen storage and dye assembly," *Angew. Chem.*, 119:6758-62, 2007.

Férey, "Hybrid porous solids: past, present, future," *Chem. Soc. Rev.*, 37:191-214, 2008.

Hermes, et al., "Selective nucleation and growth of metal-organic open framework thin films on patterned COOH/CF3-terminated self-assembled monolayers on Au(111)," *J. Am. Chem. Soc.*, 127:13744-5, 2005.

Hou, et al., "Porous metal-organic framework based on mu4-oxo tetrazinc clusters: sorption and guest-dependent luminescent properties," *Inorg. Chem.*, 47:1346-51, 2008.

Huang, et al., "Shape-selective sorption and fluorescent sensing of aromatics in a flexible network of tetrakis[(4-methylthiophenyl)ethynyl]silane and AgBF$_4$," *Chem. Mater.*, 21:541-6, 2009.

Hwang, et al., "Amine grafting on coordinatively unsaturated metal centers of MOFs: consequences for catalysis and metal encapsulation," *Angew. Chem. Int. Ed.*, 47:4144-8, 2008.

Kesanli, et al., "Highly interpenetrated metal-organic frameworks for hydrogen storage," *Angew. Chem. Int. Ed. Engl.*, 44:72-5, 2004.

Kitagawa, et al., "Functional porous coordination polymers," *Angew. Chem. Int. Ed.*, 43:2334-75, 2004.

Koder, et al., "Design and engineering of an O$_2$ transport protein," *Nature*, 458:305-9, 2009.

Koh, et al., "A porous coordination copolymer with over 5000 m2/g BET surface area," *J. Am. Chem. Soc.*, 131:4184-5, 2009.

Lan, et al., "A luminescent microporous metal-organic framework for the fast and reversible detection of high explosives," *Angew. Chem. Int. Ed.*, 48:2334-8, 2009.

Lee, et al., "A comparison of the H2 sorption capacities of isostructural metal-organic frameworks with and without accessible metal sites: [{Zn2(abtc)(dmf)2}3] and [{Cu2(abtc)(dmf)2}3] versus [{Cu2(abtc)}3]," *Agnew. Chem. Int. Ed.*, 47:7741-5, 2008.

Li, et al., "Design and synthesis of an exceptionally stable and highly porous metal-organic framework," *Nature*, 402:276-9, 1999.

Lim, et al., "Cucurbit[6]uril: organic molecular porous material with permanent porosity, exceptional stability, and acetylene sorption properties," *Agnew. Chem.*, 120:3400-03, 2008.

Lin, et al., "High capacity hydrogen adsorption in Cu(II) tetracarboxylate framework materials: the role of pore size, ligand functionalization, and exposed metal sites," *J. Am. Chem. Soc.*, 131:2159-71, 2009.

Lin, et al., "Hydrogen, methane and carbon dioxide adsorption in metal-organic framework materials," *Top Curr. Chem.*, 293:35-76, 2010.

Lin, et al., "Modular synthesis of functional nanoscale coordination polymers," *Angew. Chem. Int. Ed.*, 48:650-8, 2009.

Liu, et al., "Increasing the density of adsorbed hydrogen with coordinatively unsaturated metal centers in metal-organic frameworks," *Langmuir*, 24:4772-7, 2008.

Liu, et al., "Metal-organic framework as a template for porous carbon synthesis," *J. Am. Chem. Soc.*, 130:5390-1, 2008.

Ma and Lin, "Unusual interlocking and interpenetration lead to highly porous and robust metal-organic frameworks," *Angew. Chem. Int. Ed.*, 48:3637-40, 2009.

Ma, et al., "Further investigation of the effect of framework catenation on hydrogen uptake in metal-organic frameworks," *J. Am. Chem. Soc.*, 130:15896-902, 2008.

Ma, et al., "Metal-organic framework from an anthracene derivative containing nanoscopic cages exhibiting high methane uptake," *J. Am. Chem. Soc.*, 130:1012-6, 2008.

Matsuda, et al., "Highly controlled acetylene accommodation in a metal-organic microporous material," *Nature*, 436:238-41, 2005.

Millward and Yaghi, "Metal-organic frameworks with exceptionally high capacity for storage of carbon dioxide at room temperature," *J. Am. Chem. Soc.*, 127:17998-9, 2005.

Morris and Wheatley, "Gas storage in nanoporous materials," *Angew. Chem. Int. Ed.*, 47:4966-81, 2008.

Nelson, et al., "Supercritical processing as a route to high internal surface areas and permanent microporosity in metal-organic framework materials," *J. Am. Chem. Soc.*, 131:458-60, 2009.

Noro, et al., "A new, methane adsorbent, porous coordination polymer," *Angew. Chem. Int. Ed. Engl.*, 39:2081-4, 2000.

Park, et al., "Exceptional chemical and thermal stability of zeolitic imidazolate frameworks," *Proc. Natl. Acad. Sci. USA*, 103:10186-91, 2006.

Reid and Thomas, "Adsorption kinetics and size exclusion properties of probe molecules for the selective porosity in a carbon molecular sieve used for air separation," *J. Phys. Chem. B.*, 105:10619-29, 2001.

Reid and Thomas, "Adsorption of gases on a carbon molecular sieve used for air separation: linear adsorptives as probes for kinetic selectivity," *Langmuir*, 15:3206-18, 1999.

Rosi, et al., "Hydrogen storage in microporous metal-organic frameworks," *Science*, 300:1127-9, 2003.

Rosi, et al., "Rod packings and metal-organic frameworks constructed from rod-shaped secondary building units," *J. Am. Chem. Soc.*, 127:1504-18, 2005.

Roswell and Yaghi, "Effects of functionalization, catenation, and variation of the metal oxide and organic linking units on the low-pressure hydrogen adsorption properties of metal-organic frameworks," *J. Am. Chem. Soc.*, 128:1304-15, 2006.

Samsonenko, et al., "Microporous magnesium and manganese formates for acetylene storage and separation," *Chem. Asian J.*, 2:484-8, 2007.

Seo, et al., "A homochiral metal-organic porous material for enantioselective separation and catalysis," *Nature*, 404:982-6, 2000.

Serre, et al., "Role of solvent-host interactions that lead to very large swelling of hybrid frameworks," *Science*, 315:1828-31, 2007.

Shimomura, et al., "Porous coordination polymers towards gas technology," *Struct. Bond*, 132:51-86, 2009.

Stang and Diederich, In: *Modern Acetylene Chemistry*, VCH, New York, 1995.

Tanaka, et al., "Storage and sorption properties of acetylene in jungle-gym-like open frameworks," *Chem. Asian J.*, 3:1343-9, 2008.

Thallapally, et al., "Acetylene absorption and binding in a nonporous crystal lattice," *Angew. Chem. Int. Ed. Engl.*, 45:6506-9, 2006.

Thallapally, et al., "Flexible (breathing) interpenetrated metal-organic frameworks for CO$_2$ separation applications," *J. Am. Chem. Soc.*, 130:16842-3, 2008.

Thomas, "Adsorption and desorption of hydrogen on metal—organic framework materials for storage applications: comparison with other nanoporous materials," *Dalton Trans.*, 1487-1505, 2009.

Thomas, "How far is the concept of isolated active sites valid in solid catalysts?" *Top Catal.*, 50:98-105, 2008.

Vitillo, et al., "Role of exposed metal sites in hydrogen storage in MOFs," *J. Am. Chem. Soc.*, 130:8386-96, 2008.

Wang, et al., "Enhancing H$_2$ uptake by "close-packing" alignment of open copper sites in metal-organic framework," *Angew. Chem. Int. Ed.*, 47:7263-6, 2008.

Welbes and Borovik, "Confinement of metal complexes within porous hosts: development of functional materials for gas binding and catalysis," *Acc. Chem. Res.*, 38:765-74, 2005.

Wu, et al., "High-capacity methane storage in metal-organic frameworks M2(dhtp): the important role of open metal sites," *J. Am. Chem. Soc.*, 131:4995-5000, 2009.

Xiang, et al., "Exceptionally high acetylene uptake in a microporous metal—organic framework with open metal sites," *J. Am. Chem. Soc.*, 131:12415-9, 2009.

Xu, et al., "Robust metal-organic framework enforced by triple-framework interpenetration exhibiting high H2 storage density," *Inorg. Chem.*, 47:6825-8, 2008.

Xue, et al., "New prototype isoreticular metal—organic framework Zn$_4$O(FMA)$_3$ for gas storage," *Inorg. Chem.*, 48:4649-51, 2009.

Xue, et al., "Structure, hydrogen storage, and luminescence properties of three 3D metal-organic frameworks and NbO and PtS topologies," *Crystal Growth & Design*, 8:2478-83, 2008.

(56) References Cited

OTHER PUBLICATIONS

Yildirim and Hartman, "Direct observation of hydrogen adsorption sites and nanocage formation in metal-organic frameworks," *Phys. Rev. Lett.*, 95:215504, 2005.

Zhang and Chen, "Exceptional framework flexibility and sorption behavior of a multifunctional porous cuprous triazolate framework," *J. Am. Chem. Soc.*, 130:6010-7, 2008.

Zhang and Chen, "Optimized acetylene/carbon dioxide sorption in a dynamic porous crystal," *J. Am. Chem. Soc.*, 131:5516-21, 2009.

Zhang and Kitagawa, "Supramolecular isomerism, framework flexibility, unsaturated metal center, and porous property of Ag(I)/Cu(I) 3,3',5,5'-tetrametyl-4,4'-bipyrazolate," *J. Am. Chem. Soc.*, 130:907-17, 2008.

Zhang, et al., "A highly connected porous coordination polymer with unusual chnnel structure and sorption properties," *Angew. Chem. Int. Ed.*, 48:5287-90, 2009.

Zhang, et al., "Versatile structure-direction roles of deep-eutectic solvents and their implication in the generation of porosity and open metal sites for gas storage," *Angew. Chem. Int. Ed.*, 48:3486-90, 2009.

Zhang, et al., "Zeolitic boron imidazolate frameworks," *Angew. Chem. Int. Ed. Engl.*, 48:2542-5, 2009.

Zhao, et al., "Hysteretic adsorption and desorption of hydrogen by nanoporous metal-organic frameworks," *Science*, 306:1012-5, 2004.

Zhou and Yildirim, "Nature and tunability of enhanced hydrogen binding in metal-organic frameworks with exposed transition metal sites," *J. Phys. Chem. C*, 112:8132, 2008.

Zhou, et al., "Enhanced H2 adsorption in isostructural metal-organic frameworks with open metal sites: strong dependence of the binding strength on metal ions," *J. Am. Chem. Soc.*, 130:15268-9, 2008.

Dybtsev, et al., "A homochiral metal-organic material with permanent porosity, enantioselective sorption properties, and catalytic activity," *Angew. Chem. Int. Ed.*, 45:916-920, 2006.

Hu, et al., "A new MOF-505 analog exhibiting high acetylene storage," *Chem. Commun.*, pp. 7551-7553, 2009.

McKinlay, et al., "Exceptional behavior over the whole adsorption-storage-delivery cycle for NO in porous metal organic frameworks," *J. Am. Chem. Soc.*, 130:10440-10444, 2008.

Banerjee, et al., "Control of pore size and functionality in isoreticular zeolitic imidazolate frameworks and their carbon dioxide selective capture properties," *J. Am. Chem. Soc.*, 131:3875-7, 2009.

Chen, et al., "Metal-organic frameworks with functional pores for recognition of small molecules," *Acc. Chem. Res.*, 43:1115-24, 2010.

International Search Report and Written Opinion, issued in PCT/US2010/023773, dated Apr. 1, 2010.

Spek, "Single-crystal structure validation with the program PLATON," *J. AppL Cryst.*, 36:7-13, 2003.

Tanaka, et al., "Anthracene array-type porous coordination polymer with host-guest charge transfer interactions in excited states," *Chem. Commun.*, pp. 3142-3144, 2007.

Xiang, et al., "Open metal sites within isostructural metal-organic frameworks for differential recognition of acetylene and extraordinarily high acetylene storage capacity at room temperature," *Angew. Chem. Int. Ed. Engl.*, 49:4615-8, 2010.

Babarao, et al., "Storage and seaparation of CO2 and CH4 in silicalite, C168 schwarzite, and IRMOF-1: a comparative study from Monte Carlo simulation," *Langmuir*, 23:659-66, 2007.

Bai, et al., "The designed assembly of augmented diamond networks from predetermined pentanuclear tetrahedral units," *Angew. Chem. Int. Ed. Engl.*, 47:5344-7, 2008.

Busker, et al., "Isomer-selective vibrational spectroscopy of benzene-acetylene aggregates: comparison with the structure of the bezene-acetylene cocrystal," *Angew. Chem. Int. Ed. Engl.*, 47:10094-7, 2008.

Caskey, et al., "Dramatic tuning of carbon dioxide uptake via metal substitution in a coordination polymer with cylindrical pores," *J. Am. Chem. Soc.*, 130:10870-1, 2008.

Chen, et al., "A microporous metal-organic framework for gas-chromatographic separation of alkanes," *Angew. Chem. Int. Ed. Engl.*, 45:1390-3, 2006.

Couck, et al., "An anime-functionalized MIL-53 metal-organic framework with large separation power for CO2 and CH4," *J. Am. Chem. Soc.*, 131:6326-7, 2009.

Czepirski and Jagiello, "Virial-Type Thermal Equation of Gas-Solid Adsorption," *Chem. Eng. Sci.*, 44:797-801, 1989.

Eddaoudi, et al., "Porcus metal-organic polyhedra: 25 A cuboctoahedron constructed from 12 Cu2(CO2)4 paddle-wheel building blocks," *J. Am. Chem. Soc.*, 123:4368-9, 2001.

Fang, et al., "A multifunctional metal-organic open framework with a bcu topology constructed from undecanuclear clusters," *Angew. Chem.*, 118:6272-6, 2006.

Fang, et al., "Microporous metal-organic framwork constructed from heptanuclear zinc carboxylate secondary building units" *Chem. Eur. J.*, 12:3754-8, 2006.

Férey, et al., "Hydrogen adsorption in the nanoporous metal-benzenedicarboxylate $M(OH)(O2C-C6H4-CO2)$ ($M=Al3+$, $Cr3+$), MIL-53," *Chem. Commun.*, pp. 2976-2977, 2003.

Furukawa, et al., "Independent verification of the saturation hydrogen uptake in MOF-177 and establishment of a benchmark for hydrogen adsorption in metal-organic frameworks," *J. Mater. Chem.* 17:3197-204, 2007.

Jagiello, et al., "Adsorption near ambient temperatures of methane, carbon tetrafluoride, and sulfur hexafluoride on commerical activated carbons," *J. Chem. Eng. Data*, 40:1288, 1995.

Lee, et al., "Synthesis and gas sorption properties of a metal-azolium framework material," *Inorg. Chem.*, 48:9971-3, 2009.

Ma, et al., "Framework-Catenation Isomerism in MOFs and Its Impact on Hydrogen Uptake," *J. Am. Chem. Soc.*, 129:1858-9, 2007.

Mu, et al., "A novel metal-organic coordination polymer for selective adsorption of $CO_2$ over $CH_4$," *Chem. Commun.*, pp. 2493-2495, 2009.

Mulfort and Hupp, "Chemical reduction of metal-organic framework materials as a method to enhance gas uptake and binding," *J. Am. Chem. Soc.*, 129:9604-5, 2007.

Myers and Prausnitz, "Thermodynamics of mixed-gas adsorption," *AIChE J.*, 11:121-7, 1965.

Rieter, et al., "Nanoscale coordination polymers for platinum-based anticancer delivery," *J. Am. Chem. Soc.*, 130:11584-5, 2008.

Wang, et al., "Bottom-up synthesis of porous coordination frameworks: apical substitution of a pentanuclear tetrahedral precursor," *Angew. Chem. Int. Ed.*, 48:5291-5, 2009.

Xiao, et al., "High-capacity hydrogen and nitric oxide adsorption and storage in a metal-organic framework," *J. Am. Chem. Soc.*, 129:1203-9, 2007.

Xie, et al., "Porous coordination polymer with flexibility imparted by coordinatively changeable lithium ions on the pore surface," *Inorg. Chem.*, 49:1158-65, 2010.

Yang and Zhong, "Molecular simulation of carbon dioxide/methane/hydrogen mixture adsorption in metal-organic frameworks,"*J. Phys. Chem. B.*, 110:17776-83, 2006.

* cited by examiner

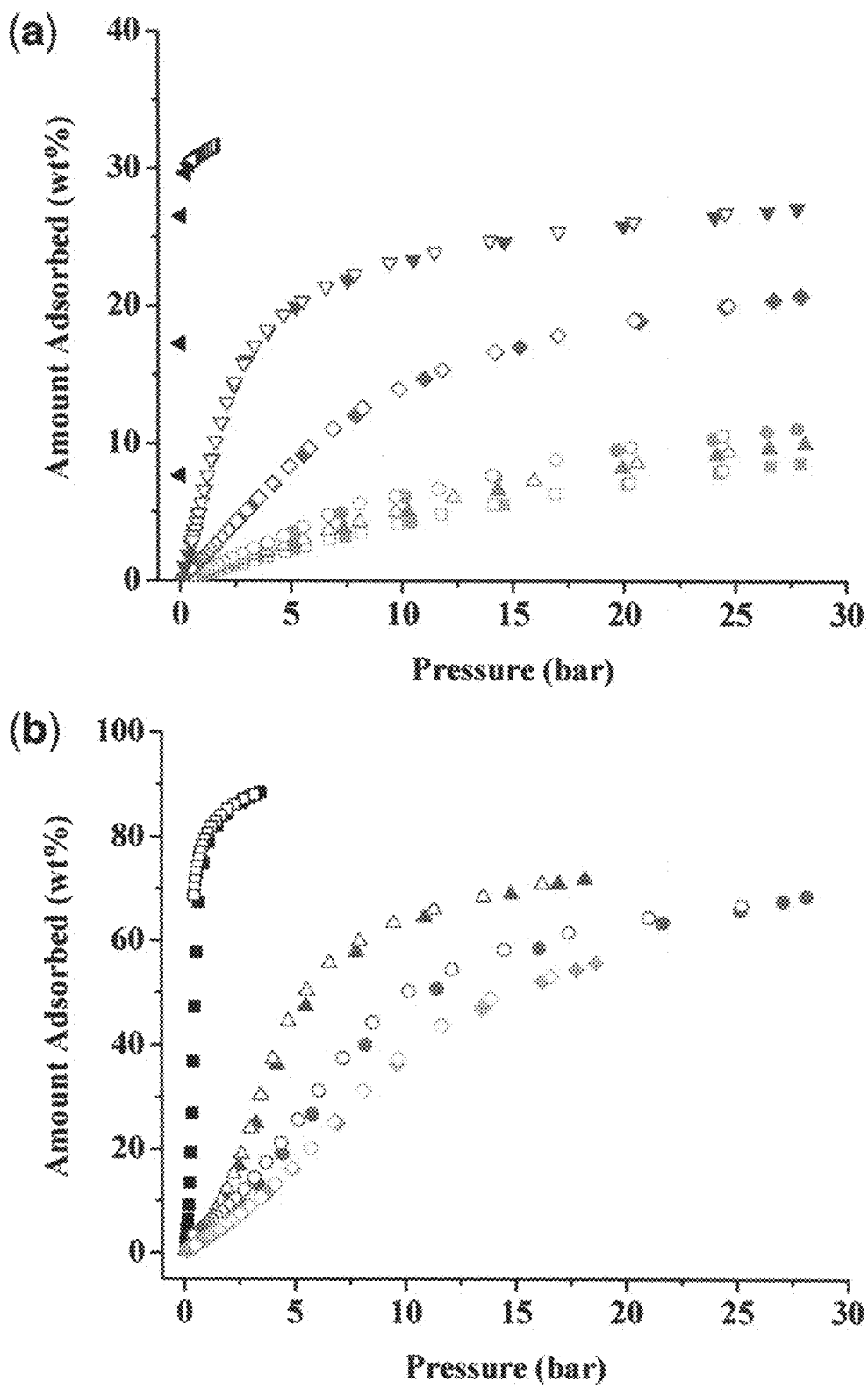
FIGS. 3(a)-(b)

ISORETICULAR METAL-ORGANIC FRAMEWORK OF THE FORMULA $ZN_4O(FMA)_3$

The present application claims priority to U.S. Provisional Application Ser. No. 61/343,324, filed Apr. 27, 2010, the entire contents of which is incorporated herein by reference in its entirety.

This invention was made with government support under grant number CHE 0718281 from the National Science Foundation. The government has certain rights in the invention.

BACKGROUND OF THE INVENTION

I. Field of the Invention

The present disclosure relates generally to the fields of chemistry and materials science. More particularly, it concerns metal-organic frameworks, compositions thereof and methods use thereof, including for gas storage, gas separation, catalysis and sensing.

II. Description of Related Art

With the realization of open structures and permanent porosity in some prototype metal-organic frameworks (MOFs) such as MOF-5 (IRMOF-1) and HKUST-1 (Li et al., 1999; Chui et al., 1999), research attention has focused on the synthesis and design of MOFs with improved characteristics for applications such as gas storage, gas separation, catalysis, and sensing (Li et al., 1999; Eddaoudi et al., 2002; Eddaoudi et al., 2008; Chui et al., 1999; Chen et al., 2005; Zhao et al., 2004; Ma et al., 2008; Chandler et al., 2006; Seo et al., 2000; Dinca and Long, 2008; Nelson et al., 2009; Kesanli et al., 2005; Hou et al., 2008; Zhang and Chen, 2008; Lin et al., 2009; Zhang et al., 2009; Lan et al., 2009; Huang et al., 2009; Chen et al., 2007; Chen et al., 2008a; Chen et al., 2008b; Rowsell et al., 2006; Millward et al., 2005; Rosi et al., 2003; Serre et al., 2007; Koh et al., 2009; Noro et al., 2000; Bourrelly et al., 2005; Ma et al., 2008; Fang et al., 2007; Xue et al., 2008a; Xue et al., 2008b; Hermes et al., 2005). With the improved synthesis of IRMOF-1 by solvothermal methodology, IRMOF-1 has been one of the most examined prototype MOFs. IRMOF-1 exhibits high porosity and is a promising gas storage material (Rowsell et al., 2006; Millward et al., 2005; Rosi et al., 2003). IRMOF-1 has also been explored as a template to design new catalysts and porous carbon materials (Hermes et al., 2005; Liu et al., 2008). A series of IRMOFs of diverse porosity have also been developed.[20] Longer bicarboxylates have lead to interpenetrated IRMOFs and quite flexible noninterpenetrated ones; however, except for IRMOF-20, most of these were not very porous (Rowsell et al., 2006; Millward et al., 2005; Rosi et al., 2003). In the case of IRMOF-20, the limited availability and cost of thieno[3,2-b]thiophene-2,5-dicarboxylate imposes limits on the usefulness of IRMOF-20 for many applications. Accordingly, identifying and developing materials and compositions that overcome these limitations is desirable.

SUMMARY OF THE INVENTION

Disclosed herein is are new metal organic framework based on the formula $[Zn_4O(FMA)_3]_n$, compositions thereof and methods use thereof, including for gas storage, gas separation, catalysis and sensing. In one aspect there is provided a metal-organic framework (MOF) comprising a repeat unit of the formula $Zn_4O(fumarate)_3$. In some embodiments, the MOF further comprises one or more solvent molecules. In some embodiments, one or more of the solvent molecules is independently selected from the group consisting of N,N'-dimethylformamide, N,N'-dimethylformamide and ethanol.

In other embodiments, the MOF is substantially free from any solvent molecules. In some embodiments, the MOF has a weight percentage at least 90%, 95% or 99% attributable to repeat units of the formula $Zn_4O(fumarate)_3$.

In another aspect, there is provided a method of storing gas comprising:

(a) obtaining a metal-organic framework (MOF) comprising a repeat unit of the formula $Zn_4O(fumarate)_3$;

(b) combining the MOF with a gas.

In some embodiments, the MOF further comprises one or more solvent molecules. In some embodiments, one or more of the solvent molecules are independently selected from the group consisting of N,N'-dimethylformamide, N,N'-dimethylformamide and ethanol. In other embodiments, the MOF is substantially free from any solvent molecules. In some embodiments, the MOF has a weight percentage at least 90%, 95% or 99% attributable to repeat units of the formula $Zn_4O$ $(fumarate)_3$.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

FIGS. 3(a)-(b). Methane and Carbon Dioxide Adsorption/Desorption Isotherms of $Zn_4O(FMA)_3$. The two graphs show methane adsorption (FIG. 3(a)) and carbon dioxide adsorption (FIG. 3(b)) as a function of pressure and temperature. For FIG. 3(a), the data points correspond as follows: 125 K (black triangles), 200 K (blue triangles), 240 K (green diamonds), 280 K (magenta circles), 290 K (red triangles), and 300 K (orange circles). For FIG. 3(b), the data points correspond as follows: 220K (black squares), 280K (blue triangles), 300 K (green circles), and 310 K (orange diamonds). In both, filled circles correspond to adsorption, and open circles correspond to desorption.

DESCRIPTION OF ILLUSTRATIVE EMBODIMENTS

Figure 1:
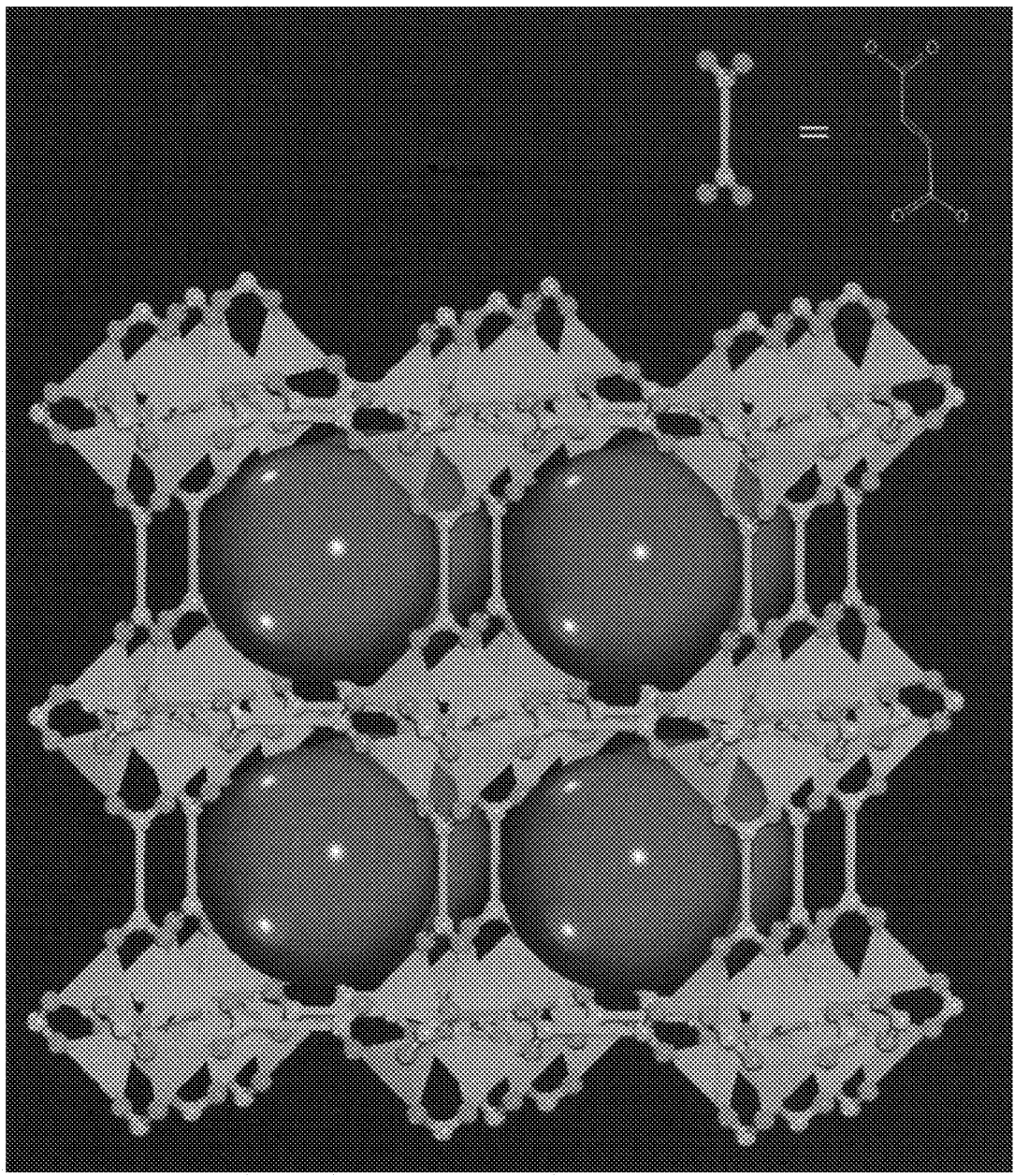
FIG. 1. X-Ray Crystal Structure of $Zn_4O(FMA)_3$. The structure shows a cubic net of intersecting pores of about 6.8×6.8 Å (Zn, pink; O, red).

Disclosed herein is are new metal organic framework having repeat units of the formula $Zn_4O(FMA)_3$. Also disclosed are compositions thereof and methods use thereof, including for gas storage, gas separation, catalysis and sensing.

I. Definitions

FMA refers to the fumarate dianion.

"Guest molecules" refer to solvent molecules, including, for example, water, N,N'-dimethylformamide, N,N'-diethylformamide and ethanol.

"Metal-organic frameworks" (MOFs) are framework materials self-assembled by the coordination of metal ions with organic linkers exhibiting porosity, typically established by gas adsorption. The MOFs discussed and disclosed herein are at times simply identified by their repeat unit (see below), that is without brackets or the subscript n.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc.

"IRMOF" refers to an iso-reticular metal-organic framework. For example, IRMOF-1 (MOF-5) is based on a three-dimensional cubic structure having the repeat unit $Zn_4O$ $(BDC)_3$ where BDC is benzene-1,4-dicarboxylate.

MOF-5 corresponds to the formula $[Zn_4O(BDC)_3]_n$ where BDC and n are defined as above.

"Pores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Interpenetrating metal-organic framework" is defined as metal-organic frameworks interlocked with each other.

"Multidentate organic linker" is defined as ligand having several binding sites for the coordination to one or more metal ions.

When used in the context of a chemical group, "hydrogen" means —H; "hydroxy" means —OH; "oxo" means =O; "halo" means independently —F, —Cl, —Br or —I; "amino" means —$NH_2$ (see below for definitions of groups containing the term amino, e.g., alkylamino); "hydroxyamino" means —NHOH; "nitro" means —$NO_2$; imino means =NH (see below for definitions of groups containing the term imino, e.g., alkylimino); "cyano" means —CN; "azido" means —$N_3$; in a monovalent context "phosphate" means —OP(O) $(OH)_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —$SiH_3$ (see below for definitions of group(s) containing the term silyl, e.g., alkylsilyl).

The symbol "—" means a single bond, "=" means a double bond, and "≡" means triple bond. The symbol "=== " represents a single bond or a double bond. The symbol " ～～～ ", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀━" means a single bond where the group attached to the thick end of the wedge is "out of the page." The symbol " ⦀⦀⦀ " means a single bond where the group attached to the thick end of the wedge is "into the page". The symbol "～～～" means a single bond where the conformation is unknown (e.g., either R or S), the geometry is unknown (e.g., either E or Z) or the compound is present as mixture of conformation or geometries (e.g., a 50%/50% mixture).

For the groups below, the following parenthetical subscripts further define the groups as follows: "(Cn)" defines the exact number (n) of carbon atoms in the group. "(C≤n)" defines the maximum number (n) of carbon atoms that can be in the group, with the minimum number of carbon atoms in such at least one, but otherwise as small as possible for the group in question, e.g., it is understood that the minimum number of carbon atoms in the group "alkenyl$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —$CH_3$ (Me), —$CH_2CH_3$ (Et), —$CH_2CH_2CH_3$ (n-Pr), —$CH(CH_3)_2$ (iso-Pr), —$CH(CH_2)_2$ (cyclopropyl), —$CH_2CH_2CH_2CH_3$ (n-Bu), —$CH(CH_3)$ $CH_2CH_3$ (sec-butyl), —$CH_2CH(CH_3)_2$ (iso-butyl), —$C(CH_3)_3$ (tert-butyl), —$CH_2C(CH_3)_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —$CH_2OH$, —$CH_2Cl$, —$CH_2Br$, —$CH_2SH$, —$CF_3$, —$CH_2CN$, —$CH_2C(O)H$, —$CH_2C(O)$ OH, —$CH_2C(O)OCH_3$, —$CH_2C(O)NH_2$, —$CH_2C(O)$ $NHCH_3$, —$CH_2C(O)CH_3$, —$CH_2OCH_3$, —$CH_2OCH_2CF_3$, —$CH_2OC(O)CH_3$, —$CH_2NH_2$, —$CH_2NHCH_3$, —$CH_2N$ $(CH_3)_2$, —$CH_2CH_2Cl$, —$CH_2CH_2OH$, —$CH_2CF_3$, —$CH_2CH_2OC(O)CH_3$, —$CH_2CH_2NHCO_2C(CH_3)_3$, and —$CH_2Si(CH_3)_3$.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH═CH$_2$ (vinyl), —CH═CHCH$_3$, —CH═CHCH$_2$CH$_3$, —CH$_2$CH═CH$_2$ (allyl), —CH$_2$CH═CHCH$_3$, and —CH═CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH═CHF, —CH═CHCl and —CH═CHBr, are non-limiting examples of substituted alkenyl groups.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "aryl" when used without the "substituted" modifier refers to a monovalent group with an aromatic carbon atom as the point of attachment, said carbon atom forming part of one or more six-membered aromatic ring structure(s) wherein the ring atoms are all carbon, and wherein the monovalent group consists of no atoms other than carbon and hydrogen. Non-limiting examples of aryl groups include phenyl (Ph), methylphenyl, (dimethyl)phenyl, —C$_6$H$_4$CH$_2$CH$_3$ (ethylphenyl), —C$_6$H$_4$CH$_2$CH$_2$CH$_3$ (propylphenyl), —C$_6$H$_4$CH(CH$_3$)$_2$, —C$_6$H$_4$CH(CH$_2$)$_2$, —C$_6$H$_3$(CH$_3$)CH$_2$CH$_3$ (methylethylphenyl), —C$_6$H$_4$CH═CH$_2$ (vinylphenyl), —C$_6$H$_4$CH═CHCH$_3$, —C$_6$H$_4$C≡CH, —C$_6$H$_4$C≡CCH$_3$, naphthyl, and the monovalent group derived from biphenyl. The term "substituted aryl" refers to a monovalent group with an aromatic carbon atom as the point of attachment, said carbon atom forming part of one or more six-membered aromatic ring structure(s) wherein the ring atoms are all carbon, and wherein the monovalent group further has at least one atom independently selected from the group consisting of N, O, F, Cl, Br, I, Si, P, and S, Non-limiting examples of substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NHCH$_3$, —C$_6$H$_4$N(CH$_3$)$_2$, —C$_6$H$_4$CH$_2$OH, —C$_6$H$_4$CH$_2$OC(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, and —C$_6$H$_4$CON(CH$_3$)$_2$.

The term "heteroaryl" when used without the "substituted" modifier refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group consists of no atoms other than carbon, hydrogen, aromatic nitrogen, aromatic oxygen and aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, chromenyl (where the point of attachment is one of the aromatic atoms), and chromanyl (where the point of attachment is one of the aromatic atoms). The term "substituted heteroaryl" refers to a monovalent group with an aromatic carbon atom or nitrogen atom as the point of attachment, said carbon atom or nitrogen atom forming part of an aromatic ring structure wherein at least one of the ring atoms is nitrogen, oxygen or sulfur, and wherein the monovalent group further has at least one atom independently selected from the group consisting of non-aromatic nitrogen, non-aromatic oxygen, non aromatic sulfur F, Cl, Br, I, Si, and P.

The term "acyl" when used without the "substituted" modifier refers to a monovalent group with a carbon atom of a carbonyl group as the point of attachment, further having a linear or branched, cyclo, cyclic or acyclic structure, further having no additional atoms that are not carbon or hydrogen, beyond the oxygen atom of the carbonyl group. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, C(O)C$_6$H$_5$, C(O)C$_6$H$_4$CH$_3$, —C(O)C$_6$H$_4$CH$_2$CH$_3$, —COC$_6$H$_3$(CH$_3$)$_2$, and —C(O)CH$_2$C$_6$H$_5$, are non-limiting examples of acyl groups. The term "acyl" therefore encompasses, but is not limited to groups sometimes referred to as "alkyl carbonyl" and "aryl carbonyl" groups. The term "substituted acyl" refers to a monovalent group with a carbon atom of a carbonyl group as the point of attachment, further having a linear or branched, cyclo, cyclic or acyclic structure, further having at least one atom, in addition to the oxygen of the carbonyl group, independently selected from the group consisting of N, O, F, Cl, Br, I, Si, P, and S. The groups, —C(O)CH$_2$CF$_3$, —CO$_2$H (carboxyl), —CO$_2$CH$_3$ (methylcarboxyl), —CO$_2$CH$_2$CH$_3$, —CO$_2$CH$_2$CH$_2$CH$_3$, —CO$_2$C$_6$H$_5$, —CO$_2$CH(CH$_3$)$_2$, CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, —CONHCH$_2$CF$_3$, —CO-pyridyl, —CO-imidazoyl, and —C(O)N$_3$, are non-limiting examples of substituted acyl groups. The term "substituted acyl" encompasses, but is not limited to, "heteroaryl carbonyl" groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The term "substituted alkoxy" refers to the group —OR, in which R is a substituted alkyl, as that term is defined above. For example, —OCH$_2$CF$_3$ is a substituted alkoxy group.

The term "alkylamino" when used without the "substituted" modifier refers to the group —NHR, in which R is an alkyl, as that term is defined above. Non-limiting examples of alkylamino groups include: —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —NH-cyclopentyl, and —NH-cyclohexyl. The term "substituted alkylamino" refers to the group —NHR, in which R is a substituted alkyl, as that term is defined above. For example, —NHCH$_2$CF$_3$ is a substituted alkylamino group.

The term "dialkylamino" when used without the "substituted" modifier refers to the group —NRR', in which R and R' can be the same or different alkyl groups, or R and R' can be taken together to represent an alkanediyl having two or more saturated carbon atoms, at least two of which are attached to the nitrogen atom. Non-limiting examples of dialkylamino groups include: —NHC(CH$_3$)$_3$, —N(CH$_3$)CH$_2$CH$_3$, —N(CH$_2$CH$_3$)$_2$, N-pyrrolidinyl, and N-piperidinyl. The term "substituted dialkylamino" refers to the group —NRR', in which R and R' can be the same or different substituted alkyl groups, one of R or R' is an alkyl and the other is a substituted alkyl, or R and R' can be taken together to represent a substituted alkanediyl with two or more saturated carbon atoms, at least two of which are attached to the nitrogen atom.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on an atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "saturated" when referring to an atom means that the atom is connected to other atoms only by means of single bonds.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Synthetic Methods

The isoreticular metal-organic framework Zn$_4$O(FMA)$_3$.xG (FMA=fumarate; G=one or more optional guest molecules) may be made using the methods outlined in the examples section below. For example, a solvated version of the IRMOF having the repeat unit Zn$_4$O(FMA)$_3$ was synthesized by the solvothermal reaction of H$_2$FMA and Zn(NO$_3$)$_2$.6H$_2$O in N,N'-diethylformamide (DEF) at 100° C. for 24 h. This yielded a light-yellow cubic crystals formulated as Zn$_4$O(FMA)$_3$.4.5DEF.2H$_2$O by elemental microanalysis and single-crystal X-ray diffraction studies. The phase purity of the bulk material was independently confirmed by powder X-ray diffraction (PXRD) and thermal gravimetric analysis (TGA). Additional details are provided in Example 1.

These methods can be further modified, optimized and scaled up using the principles and techniques of chemistry and/or materials science as applied by a person skilled in the art. Such principles and techniques are taught, for example, in Chen et al. (2005), which is incorporated by reference herein.

III. Properties Of Mofs

Disclosed herein is the assembly of a noninterpenetrated IRMOF of a cubic net having a repeat unit of the formula Zn$_4$O(FMA)$_3$. using readily available and inexpensive starting materials, including the bicarboxylate, fumarate (FMA) (Chen et al., 2007; Serre et al., 2007). Zn$_4$O(FMA)$_3$ exhibits a rigid structure and high porosity.

One of the embodiments, an IRMOF based on the repeat unit Zn$_4$O(FMA)$_3$.4.5DEF.2H$_2$O was synthesized (Example 1) and structurally characterized by X-ray diffraction studies. The framework is composed of octahedral Zn$_4$O units that are bridged by FMA dianions to form a 3D primitive cubic (α-Po) structure with intersecting pores of ca. 6.8×6.8 Å (FIG. 1). The robustness of Zn$_4$O(FMA)$_3$.4.5DEF.2H$_2$O and its activated forms is shown in PXRD studies.

In one embodiment, an MOF based on the repeat formula Zn$_4$O(FMA)$_3$ may be used for gas storage applications. TGA studies indicate that the activated (desolvated) version, Zn$_4$O(FMA)$_3$, is thermally stable up to about 300° C. The Langmuir and Brunauer-Emmett-Teller surface areas are 1618 and 1120 m$^2$/g, respectively, based on N$_2$ adsorption at 77 K.

Figure 2:
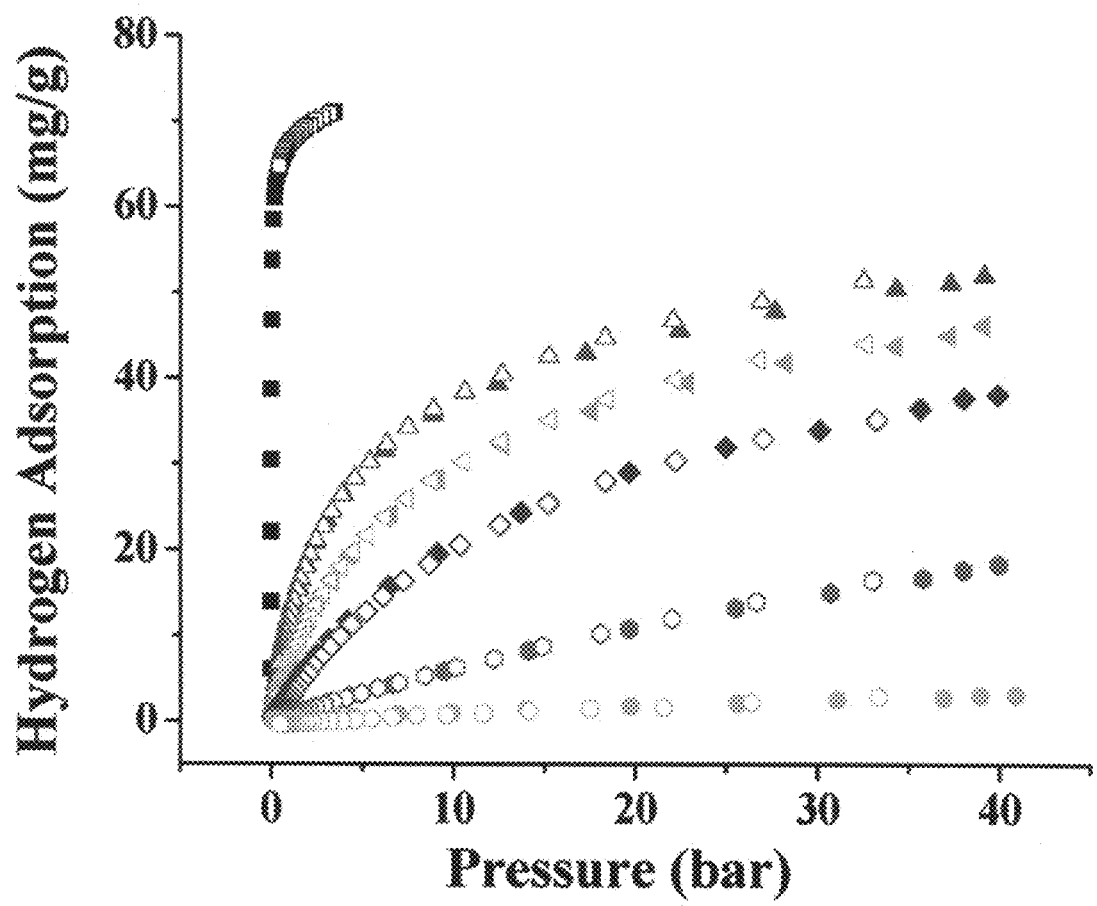
FIG. 2. Excess Hydrogen Adsorption/Desorption Isotherms of $Zn_4O(FMA)_3$. This graph shows hydrogen adsorption as a function of pressure and temperature. The data points correspond as follows: 30 K (black square), 77 K (blue triangle), 87 K (magenta triangle), 100 K (navy diamond), 150 K (green hexagon), and 300 K (orange circles). Filled circles correspond to adsorption; open circles correspond to desorption.

High-pressure gas sorption measurements were carried out at various temperatures to explore the potential of Zn$_4$O(FMA)$_3$ as a gas storage material. As shown in FIG. 2, Zn$_4$O(FMA)$_3$ takes up a large amount of H$_2$ gas, 71 mg/g, at 30 K and 3.5 bar, and 52 mg/g at 77 K and 39 bar. Given the comparatively low surface area of Zn$_4$O(FMA)$_3$, such high hydrogen storage capacities are remarkable.

Zn$_4$O(FMA)$_3$ can only adsorb a small amounts of H$_2$ gas at room temperature (0.32 wt %) at 40 bar. Zn$_4$O(FMA)$_3$ takes up a moderate amount of methane (CH$_4$) and carbon dioxide (CO$_2$) of 8.6 and 69 wt %, respectively, at 28 bar and 300 K (FIG. 3).

The coverage-dependent adsorption enthalpies of Zn$_4$O(FMA)$_3$ to H$_2$, CH$_4$, and CO$_2$ were calculated based on the virial methods (Rowsell et al., 2006; Millward et al., 2005; Rosi et al., 2003; Thomas, 2009), a well-established and reliable methodology, from fits of their adsorption isotherms at variable temperatures. Zn$_4$O(FMA)$_3$ exhibits H$_2$ adsorption enthalpies of about 4 kJ/mol (4.2 kJ/mol at the coverage of 2.85 mmol/g), which is comparable to those of other typical MOFs. The adsorption enthalpies of Zn$_4$O(FMA)$_3$ to CH$_4$ and CO$_2$ are 12.0 kJ/mol at the coverage of 5.8 mmol/g and 16.1 kJ/mol at the coverage of 8.8 mmol/g, respectively. Without being bound by theory, the open structure with intersecting pores of 6.8×6.8 Å and large cavities of about 8.5 Å within Zn$_4$O(FMA)$_3$ is consistent with no strong pore confinement effect to enhance their interactions with the small molecules examined here.

In another embodiment, Zn$_4$O(FMA)$_3$ may be used as a template for the synthesis of porous carbon materials.

IV. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Methods and Materials

Synthesis and Characterization of $Zn_4O(FMA)_3 \cdot 4.5DEF \cdot 2H_2O$: A mixture of $Zn(NO_3)_2 \cdot 6H_2O$ (0.279 g, 1.0 mmol) and $H_2FMA$ (0.116 g, 1.0 mmol) was suspended in N,N'-diethylformamide (DEF) (100 mL) and heated in a vial (400 mL) at 100° C. for 24 h. The light-yellow cubic crystals formed were collected and washed with DEF (0.34 g, 85%).

Elemental Analysis: Calcd for $Zn_4O(FMA)_3 \cdot 4.5DEF \cdot 2H_2O$ ($C_{34.5}H_{59.5}N_{4.5}O_{19.5}Zn_4$): C, 37.48; H, 5.43; N, 5.70. Found: C, 37.55; H, 5.14; N, 5.75.

Crystal data: $C_{12}H_6O_{13}Zn_4$, cubic, space group Fm3m, a=21.639 (3) Å, V=10133 (2) Å$^3$, Z=8, $D_{calc}$=0.812 g/cm$^3$, $\mu$=1.895 mm$^{-1}$, T=293 K, F(000)=2416. R1 [I>2σ(I)]=0.0688, wR2 (all data)=0.1649. CCDC 715031.

All of the methods disclosed and claimed herein can be made and executed without undue experimentation in light of the present disclosure. While the compositions and methods of this invention have been described in terms of particular embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

Bourrelly et al., *J. Am. Chem. Soc.*, 127:13519, 2005.
Chandler et al., *J. Am. Chem. Soc.*, 128:10403, 2006.
Chen et al., *Angew. Chem. Int. Ed.*, 44:4745-4749, 2005.
Chen et al., *Inorg. Chem.*, 46:1233, 2007.
Chen et al., *J. Am. Chem. Soc.*, 130:6718, 2008a.
Chen et al., *J. Am. Chem. Soc.*, 130:6411, 2008b.
Chui et al., *Science*, 283:1148, 1999.
Dinca and Long, *Angew. Chem. Int. Ed.*, 47:6766, 2008.
Eddaoudi et al., *Acc. Chem. Res.* 34:319, 2001.
Eddaoudi et al., *Science*, 295:469, 2002.
Fang et al., *Inorg. Chem.*, 47:6825, 2008.
Ferey, *Chem. Soc. Rev.*, 37:191, 2008.
Hermes et al., *J. Am. Chem. Soc.*, 127:13744, 2005.
Hou et al., *Inorg. Chem.*, 47:1346, 2008.
Huang et al., *Chem. Mater.*, 21:541, 2009.
Kesanli et al., *Angew. Chem., Int. Ed.*, 44:72, 2005.
Kitagawa et al., *Angew. Chem., Int. Ed. Engl.*, 43:2334, 2004.
Koh et al., *J. Am. Chem. Soc.*, 131:4184, 2009.
Lan et al., *Angew. Chem. Int. Ed.*, 48(19):3525-8, 2009.
Li et al., *Nature*, 402:276, 1999.
Lin et al., *J. Am. Chem. Soc.*, 131:2159, 2009.
Liu et al., *J. Am. Chem. Soc.*, 130:5390, 2008.
Ma et al., *J. Am. Chem. Soc.*, 130:1012, 2008.
Ma et al., *J. Am. Chem. Soc.*, 130:15896, 2008.
Millward et al., *J. Am. Chem. Soc.*, 127:17998, 2005.
Nelson et al., *Am. Chem. Soc.*, 131:458, 2009.
Noro et al., *Angew. Chem., Int. Ed.*, 39:1433, 2000.
Rosi et al., *Science*, 300:1127, 2003.
Rowsell et al., *J. Am. Chem. Soc.*, 128:1304, 2006.
Seo et al., *Nature*, 404:982, 2000.
Serre et al., *Science*, 315:1828, 2007.
Thomas, *Dalton Trans.*, 1487, 2009.
Zhang and Chen, *J. Am. Chem. Soc.*, 130:6010, 2008.
Zhang et al., *Angew. Chem., Int. Ed.*, 48:2542-2545, 2009.
Zhao et al., *Science*, 306:1012, 2004.

What is claimed is:

1. A metal-organic framework (MOF) comprising a repeat unit of the formula $Zn_4O(fumarate)_3$.

2. The MOF of claim 1, further comprising one or more solvent molecules.

3. The MOF of claim 2, where one or more of the solvent molecules are independently selected from the group consisting of N,N'-dimethylformamide, N,N'-dimethylformamide and ethanol.

4. The MOF of claim 1, substantially free from any solvent molecules.

5. The MOF of claim 1 having a weight percentage at least 90% attributable to repeat units of the formula $Zn_4O(fumarate)_3$.

6. The MOF of claim 1 having a weight percentage at least 95% attributable to repeat units of the formula $Zn_4O(fumarate)_3$.

7. The MOF of claim 1 having a weight percentage at least 99% attributable to repeat units of the formula $Zn_4O(fumarate)_3$.

8. A method of storing a gas comprising:
   (a) obtaining a metal-organic framework (MOF) comprising a repeat unit of the formula $Zn_4O(fumarate)_3$;
   (b) combining the MOF with a gas.

9. The method of claim 8, where the MOF further comprises one or more solvent molecules.

10. The method of claim 9, where one or more of the solvent molecules are independently selected from the group consisting of N,N'-dimethylformamide, N,N'-dimethylformamide and ethanol.

11. The method of claim 8, where the MOF has a weight percentage at least 90% attributable to repeat units of the formula $Zn_4O(fumarate)_3$.

12. The method of claim 8, where the MOF has a weight percentage at least 95% attributable to repeat units of the formula $Zn_4O(fumarate)_3$.

13. The method of claim 8, where the MOF has a weight percentage at least 99% attributable to repeat units of the formula $Zn_4O(fumarate)_3$.

* * * * *